United States Patent [19]

Shima et al.

[11] 4,255,978
[45] Mar. 17, 1981

[54] TORSIONAL VIBRATION MONITORING APPARATUS FOR A ROTATING SHAFT SYSTEM

[76] Inventors: Ichiji Shima; Tatsuo Yamamoto; Shigeru Yoshibayashi; Hiroshi Teshima, all of c/o The Kansai Electric Power Co., Inc., Technical Research Center of 2, Ichinotsubo 1-chome, Wakaoji, Amagasaki City, Osaka; Akio Hizume, 8-11, Naka-machi 1-chome, Setagaya-ku, Tokyo; Tetsuo Iki, 1998-5, Yokoo-machi, Nagasaki City, Nagasaki Prefecture; Takashi Yamamoto, 347, Motomurago, Tokitsu-cho, Nishisonogi-gun, Nagasaki Prefecture; Kyozo Kanamori, 16-10, Shiraiwa-cho, Isahaya City, Nagasaki Prefecture; Akio Shimosakoda, 37-9; Shigeho Tanaka, 39-27, both of Hokuyo-machi, Nagasaki City, Nagasaki Prefecture, all of Japan

[21] Appl. No.: 36,020

[22] Filed: May 4, 1979

[30] Foreign Application Priority Data

May 12, 1978 [JP] Japan ................................. 53-56316

[51] Int. Cl.³ .............................................. G01N 3/32
[52] U.S. Cl. .................................................... 73/577
[58] Field of Search ................. 73/650, 660, 577, 814, 73/847

[56] References Cited

U.S. PATENT DOCUMENTS

| 4,051,427 | 9/1977 | Kilgore et al. ..................... 73/650 X |
| 4,137,780 | 2/1979 | Wolfinger .............................. 73/650 |

Primary Examiner—Jerry W. Myracle

[57] ABSTRACT

A torsional vibration monitoring system for monitoring torsional vibration occurring in a rotating shaft system such as in a power generator turbine is disclosed. Torsional vibrations are measured at a small number of measurable positions on the rotating shaft system, and stresses at other arbitrary positions are estimated by linearly decomposing the torsional vibrations. The fatigue life expenditure on the rotating shaft system is obtained and monitored on the basis of the estimation obtained by the linear decomposition of the torsional vibration. For a huge vibration such as caused by thunder which may produce stresses on the rotating shaft system and which can not be estimated by the linear decomposition thereof, the torsional vibration monitoring apparatus may be provided with means to produce data which may be used in other analysis, by recording real torsional vibrations caused thereby.

3 Claims, 10 Drawing Figures

Fig.2
Fig.2A
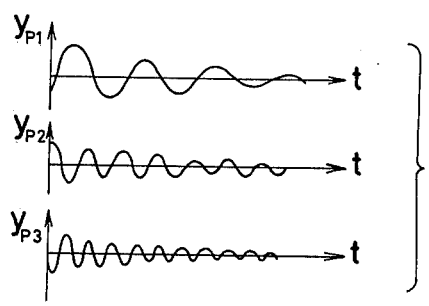
Fig.2B
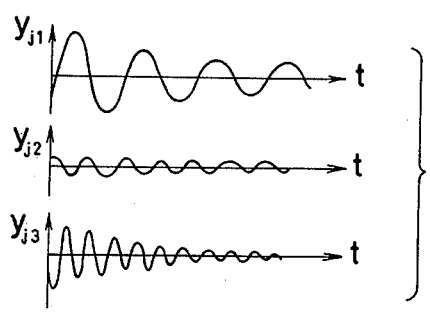
Fig.2C
Fig.2D
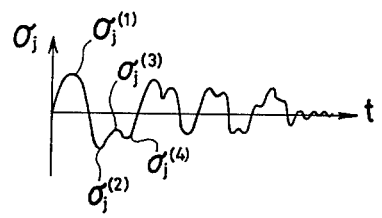
Fig.2E

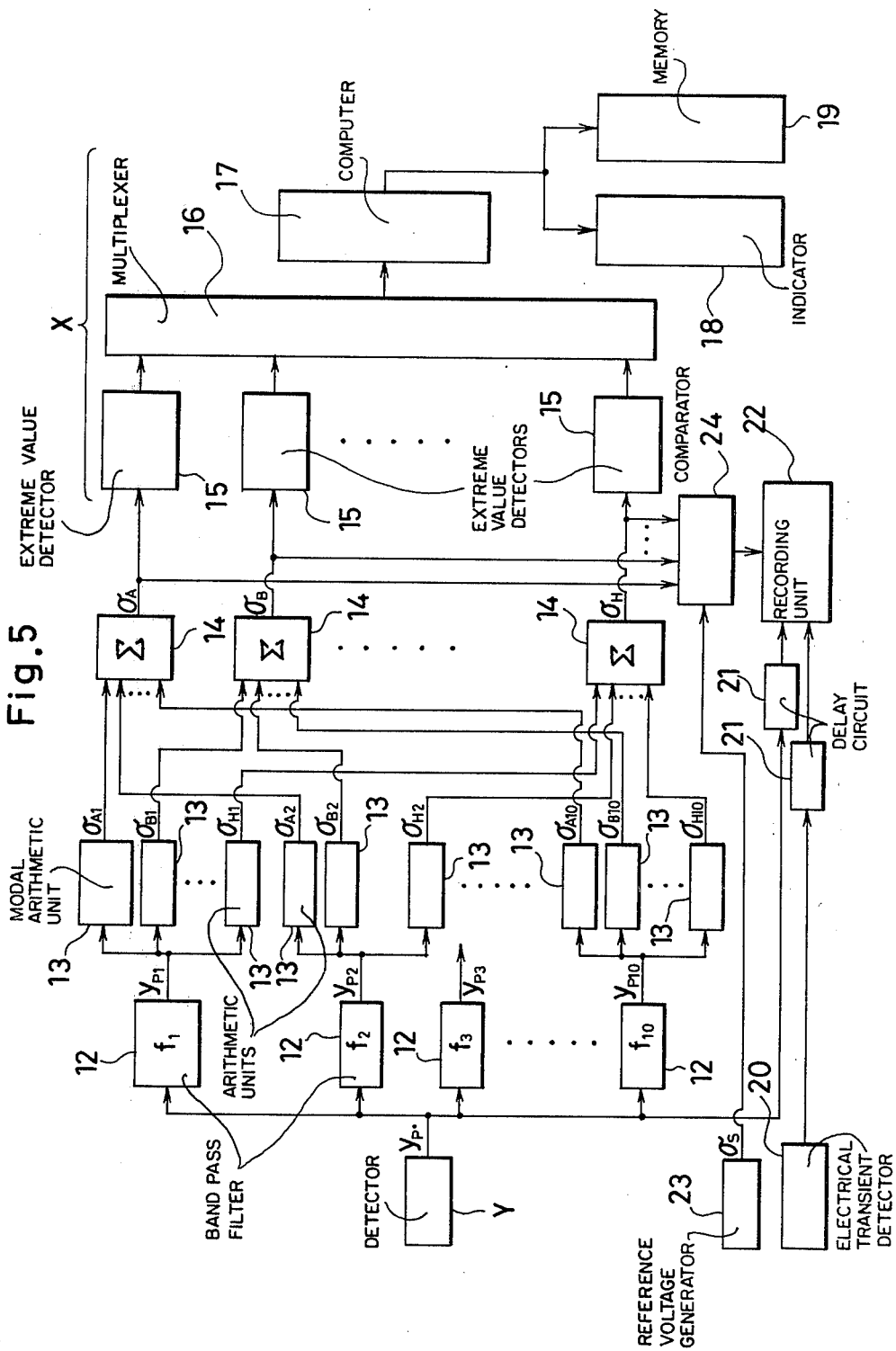

TORSIONAL VIBRATION MONITORING APPARATUS FOR A ROTATING SHAFT SYSTEM

BACKGROUND OF THE INVENTION

1. Field of the Invention

The present invention relates to a torsional vibration monitoring apparatus for monitoring torsional vibration occurring in a rotating shaft system such as for a power generator turbine, in which the torsional vibrations are measured at a small number of measurable certain positions on the rotating shaft system where the measurements are possible and stresses at other arbitrary positions thereon are estimated by linearly decomposing the measured vibrations, and the rotating shaft system is monitored on a fatigue life expenditure on the basis of the estimation obtained from the linear decomposition of the torsional vibration.

Furthermore, the present invention relates to a torsional vibration monitoring apparatus in which, when the torsional vibration whose stresses can not be estimated by the linear decomposition is produced, real torsional vibrations are recorded from which data may be obtained for other analysis.

2. Description of the Prior Art

It has been commonly recognized that, in designing a rotating shaft system such as turbine generator, compressor or marine diesel engine, it is important to exactly know various disturbances affecting the rotating shaft system. Particularly, it is very important for operators of the rotating shaft system to know a fatigue life expenditure of the rotating shaft system which may vary with the disturbance. Since, however, the length of the rotating shaft system of, for example, the turbine generator is generally very long and may become several tens meters in some cases, it is necessary to set a number of measuring positions along the rotating shaft system, causing a monitoring of the shaft system to be very difficult.

It is well known that torsional vibration occurring along the rotating shaft system must be measured because it may attribute to the fatigue and damages of the shaft system. However, it is disadvantageous economically to install torsional vibration measuring devices at a large number of positions on and along the rotating shaft system and it is sometimes impossible physically to do so.

SUMMARY OF THE INVENTION

The present invention is intended to overcome the disadvantages inherent to the conventional torsional vibration monitoring apparatus and an object of the present invention is to monitor a rotating shaft system easily, reliably and economically by measuring torsional vibrations at a small number of measurable certain positions on and along the rotating shaft system, linearly decomposing the measured results to estimate stresses at other arbitrary positions on the rotating shaft system and calculating the fatigue life expenditure of the rotating shaft system at the arbitrary positions on the basis of the estimated stresses. According to the present invention, in order to achieve the above object, a torsional vibration monitoring apparatus comprises a detector for detecting torsional vibrations at a small number of certain positions on a rotating shaft system, decomposing devices each for decomposing vibration waveforms obtained by the detector to a plurality of components of vibration modes inherent to the rotating shaft, modal arithmetic units for obtaining stresses each of different one of the vibration modes at the other arbitrary positions on the rotating shaft system on the basis of a relation between vibrations of the respective vibration modes of certain positions on the rotating shaft and the arbitrary positions thereon and a relation between the vibrations and the stresses at the arbitrary positions, adders each for adding the stresses of different one of the vibration modes obtained by the modal arithmetic units at the respective arbitrary positions and a fatigue life expenditure counting unit for calculating the fatigue life expenditure of the arbitrary positions on the rotating shaft system, due to fatigue, on the basis of the stresses at the arbitrary positions, obtained by the adders.

Another object of the present invention is to provide a torsional vibration monitoring apparatus for a rotating shaft system which is capable of preparing data for other analysis by recording real torsional vibrations in case where the vibrations occur whose stresses can not be estimated by the linear decomposition thereof. the torsional vibration monitoring apparatus comprises, in addition to the detector, the decomposing devices, modal arithmetic units and the adders, an electrical transient detector for detecting external force exerted on the rotating shaft system, a comparator for comparing the stresses at the arbitrary position obtained by the adders with a predetermined set value to provide an instruction when the stresses exceed the set value and a recording unit responsive to the instruction for recording vibration waveforms at the certain position obtained by the detector and an output of the electrical transient detector. An example of the cases where the torsional vibration on the rotating shaft system, the stress due to which can not be estimated by the linear decomposition occurs, is an unmeasurable large vibration such as thunder. In such case, according to the present invention, a real torsional vibration is recorded, which is to be analysed in more detail by using the non-linear theory and/or the plastic deformation theory to estimate the torsional vibration and the fatigue life. The recorded data may be used to determine the kind and frequency of the external force or torsional vibration thereby, and also used as materials useful in maintaining the rotating shaft system and in determination of strength design.

BRIEF DESCRIPTION OF THE DRAWINGS

FIG. 2 shows waveforms of various torsional vibrations $y_p$ occurring in the rotating shaft system, in which FIG. 2A shows the torsional vibration at a certain position P, FIG. 2B shows waveforms of i-th mode at the certain position P, where i is 1, 2, 3..., FIG. 2C shows torsional vibration waveforms of the respective modes at an arbitrary position j, which are computed from the waveforms in FIG. 2B, FIG. 2D shows a torsional vibration waveform at the position j which is a combination waveform of the waveforms in FIG. 2C and FIG. 2E shows a stress waveform at the position j;

FIG. 5 is a block diagram of the embodiment in FIG. 4.

DESCRIPTION OF THE PREFERRED EMBODIMENT

Figure 4:
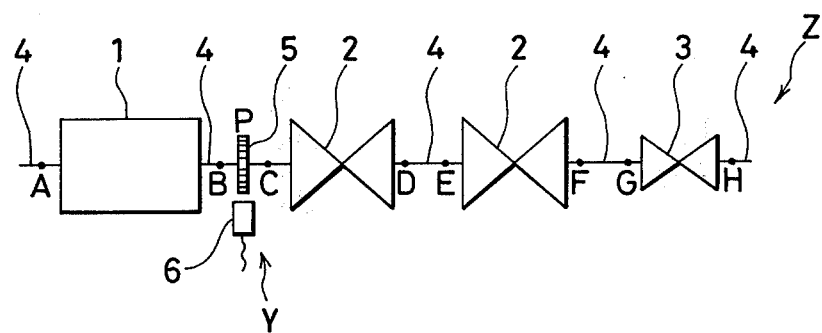
FIG. 4 is a schematic illustration of an embodiment of the present invention when applied to a turbine generator.

Referring to FIGS. 1 to 5, particularly, to FIG. 4, reference numerals 1, 2 and 3 show a generator, low pressure turbines and a high pressure turbine for driving the generator 1, respectively. A reference numeral 4 shows rotating shafts which connect each low pressure turbine 2 to the high pressure turbine 3, said rotating shafts 4 are arranged in series to constitute a rotating shaft system Z. A reference numeral 5 is a turning gear disposed between the generator 1 and one of the low pressure turbine 2. Although a plurality of turning gears 5 may be provided at each certain position P on the rotating shaft system Z, only one turning gear 5 is shown in this embodiment for simplicity of explanation, the position thereof being represented by a coordinate $x_p$. A reference numeral 6 is a pickup device for detecting a torsional vibration of the rotating shaft 4 and the pickup device 6 constitutes, together with the turning gear 5, a detector Y for transient torsional vibration of shaft. The turning gear 5 may be provided at any certain position on the rotating shaft system Z other than the position between the generator 1 and the low pressure turbine 2 and the number of the turning gears 5 may be increased if desired to increase the preciseness and reliability.

Positions A and H on each rotating shaft (4) are arbitrary positions at which estimations of the torsional vibrations of the rotating shafts are designed. The coordinate values of the positions A to H are represented by $x_A$ to $x_H$, respectively. Therefore, since the respective coordinate values x can be arbitrarily selected, the monitoring position can be freely set.

Figure 1:
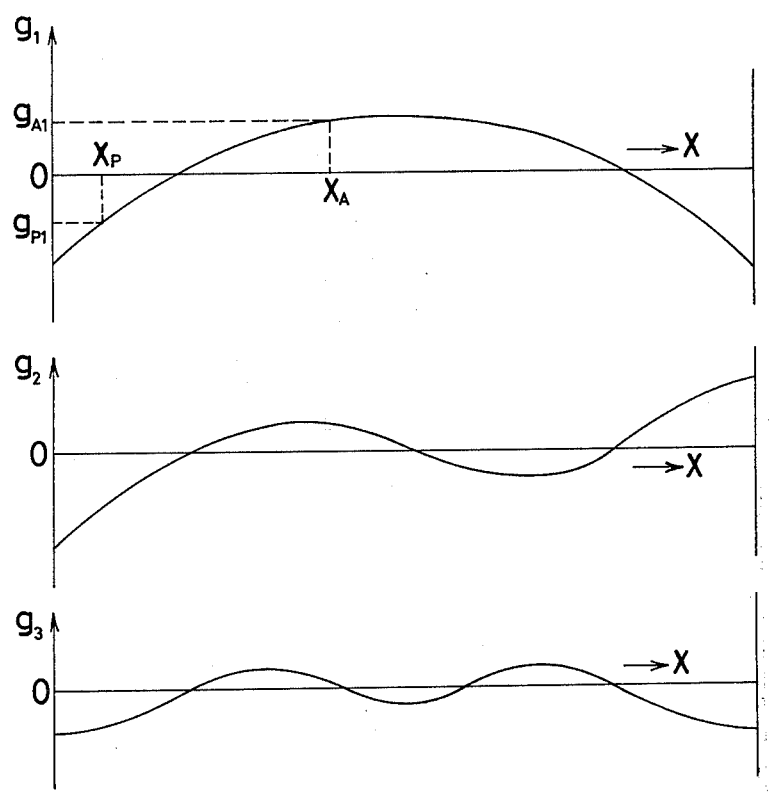
FIG. 1 in an explanatory graph showing torsional vibration modes of a rotating shaft system.
Figure 3:
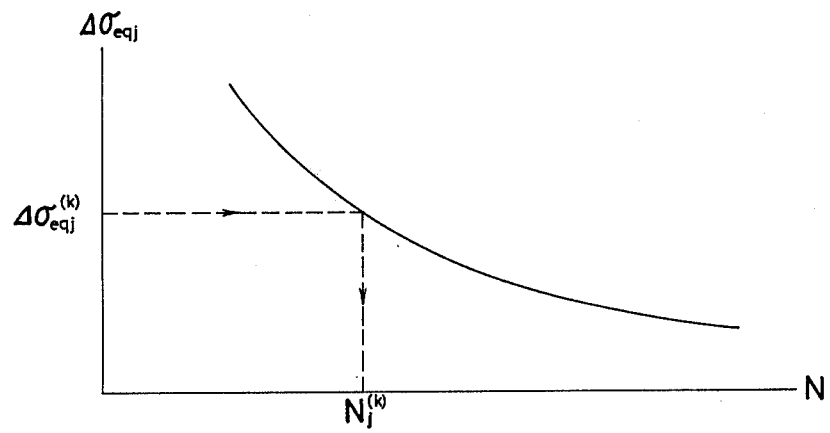
FIG. 3 is a graph showing an S-N diagram (stress magnitude-fatigue repetition number diagram)

It has been well known by those skilled in the art that the torsional vibration y of the rotating shaft system Z can be represented by using the vibration modes of the rotating shaft system Z as follows:

$$y = \Sigma y_i = \Sigma a_i g_i(x) \cos(2\pi f_i t + \epsilon_i) \quad (1)$$

where $f_i$ is an i-th specific vibration number of the rotating shaft system Z, $g_i(x)$ is an i-th vibration mode of the rotating shaft system Z which is shown in FIG. 1, $a_i$ is a component of the i-th mode, $\epsilon_i$ is phase and t is time.

Assuming that the coordinate values of the certain position P and an arbitrary position j are represented by $x_p$ and $x_j$ where j=A, B, C ...., respectively, the equation (1) can be represented as follows:

$$y_p = \Sigma y_{pi} = \Sigma a_i g_i(x_p) \cos(2\Sigma f_i t + \epsilon_i) \quad (2)$$

$$y_j = \Sigma y_{ji} = \Sigma a_i g_i(x_j) \cos(2\pi f_i t + \epsilon_i) \quad (3)$$

since $f_i$ is the i-th specific vibration number of the rotating shaft system Z, it can be previously obtained by calculation. Therefore, the torsional vibration $y_p$ at the certain position P on the rotating shaft system Z can be represented as above and a waveform at the output of the detector Y becomes as shown in FIG. 2A.

Referring to the diagram in FIG. 5, decomposing devices 12 each of which comprises a bandpass filter are connected to the detector Y. The bandpass filters 12 correspond in number to the modes $y_{pi}$ of the specific vibration number $f_i(i=1, 2, 3 ...)$ of the rotating shaft system Z and are adapted to decompose the torsional vibration wave $y_p$ detected by the detector Y into those of the respective modes $y_{pi}$. In this case, although i can be infinite theoretically, the absolute value $|g_i(x)|$ of the i-th vibration mode $g_i(x)$ becomes nearly equal to zero when i is infinite and, therefore, it may be sufficient generally to select i as equal to ten; i=10. That is, the i-th mode component $y_{pi}$ at the certain position P becomes as follows:

$$y_{pi} = a_i g_i(x_p) \cos(2\pi f_i t + \epsilon_i) \quad (4)$$

and this is shown in FIG. 2B as in cases of i=1, i=2, i=3, ..... .

As mentioned previously, $g_i(x)$ is the i-th vibration mode (function) of the rotating shaft system Z shown in FIG. 1 and can be previously obtained by calculation. Therefore, the i-th mode relation $k_{ji}$ between the certain position P and the arbitrary position j can be represented as $$k_{ji} = g_i(x_j)/g_i(x_p) \quad (5)$$

and this can be obtained previously, where k is a function. Accordingly, by combining the equations (4) and (5) with the i-th mode component at the arbitrary position j, which is $$y_{ji} = a_i g_i(x_j) \cos(2\pi f_i t + \epsilon_i),$$

$$y_{ji} = a_i k_{ji} g_i(x_p) \cos(2\pi f_i t + \epsilon_i) = k_{ji} y_{pi} \quad (6)$$

is obtained. The various mode at the arbitrary position j is shown in FIG. 2C.

Since the stress is proportional to the amplitude of vibration, the stress $\sigma_{ji}$ of the i-th mode component can be represented as $$\sigma_{ji} = a_j k_{ji} y_{pi} \quad (7)$$

where $a_j$ is a proportional constant at the arbitrary position j. That is, in FIG. 5, a reference numeral 13 shows each modal arithmetic unit for the respective modes. The number of the modal arithmetic units 13 is i and the units 13 are connected to the bandpass filters 12, respectively, the multiply the i-th mode component $y_{pi}$ (equation (4)) of the rotating shaft system Z, which is provided at the output of the bandpass filters 12 to the vibrational relation $k_{ji}$ (equation (5)) between the certain position P and the arbitrary position j and the relation $a_j$ between the vibration and the stress at the arbitrary position j to thereby obtain the i-th mode component of the stress at the arbitrary position j which is represented by the equation (7).

In FIG. 5, a reference numeral 14 shows adders. Each adder 14 is inputted with the outputs of the decomposing devices (12) concerning the i-th component to add the stresses $\sigma_{ji}$ to thereby compute the stress $\sigma_j$ at the arbitrary position j, as represented as follows:

$$\begin{aligned}\sigma_j &= \Sigma \sigma_{ji} \\ &= a_j \Sigma k_{ji} y_{pi} \\ &= a_j y_j\end{aligned} \quad (8)$$

It may be unnecessary to obtain $y_j$ in this embodiment and it is sufficient to know that it is a waveform of torsional vibration at the arbitrary position j and it takes in the form shown in FIG. 2D. The stress $\sigma_j$ at the arbitrary position j is shown by the waveform in FIG. 2E.

With the stress $\sigma_j$ at the arbitrary position j of the rotating shaft system Z determined as above, it is possible to calculate it by using the S-N diagram (stress magnitude-fatigue repetition number diagram) of material on the basis of the known fatigue life estimation. In the present invention, it is performed by the Range-pair counting method. Describing the Range-pair counting method, it is assumed that the stress at the arbitrary position j is obtained by applying the equation (8) to FIG. 2E. Furthermore assuming that extreme values in the equation (8) are represented, from that of the shortest time, by $\sigma_j(1)$, $\sigma_j(2)$ ....., a difference $\Delta\sigma_j^{(k)}$ of the stress waveform amplitude between the k-th extreme value and the (k+1)th extreme value and a mean stress $\bar{\sigma}_j^{(k)}$ thereof are represented by $$\Delta\sigma_j^{(k)} = \tfrac{1}{2}|\sigma_j^{(k)} - \sigma_j^{(k+1)}| \qquad (9)$$

$$\bar{\sigma}_j^{(k)} = \tfrac{1}{2}|\sigma_j^{(k)} + \sigma_j^{(k+1)}| \qquad (10)$$

respectively.

A stress difference $\Delta\sigma_{eqj}^{(k)}$ equivalent to the case where the mean stress is zero can be represented according to the modified Goodman chart by $$\Delta\sigma_{eqj}^{(k)} = \sigma_j^B \cdot \Delta\sigma_j^{(k)} / (\sigma_j^B - \bar{\sigma}_j^{(k)}) \qquad (11)$$

where $\sigma_j^B$ is a tension strength of the rotating shaft at the arbitrary position j thereof.

Thus, by knowing the equivalent stress difference $\Delta\sigma_{eqj}^{(k)}$ between those at the k-th and the (k+1)th extremes of the stress waveform at the arbitrary position j on the rotating shaft system Z, the number $N_j^{(k)}$ of the repetitive applications of the equivalent stress difference $\Delta_{eqj}^{(k)}$ to the arbitrary position j prior to a breakdown of the shaft can be known from the S-N diagram (FIG. 3) which shows the relation between the stress difference of the shaft material at the arbitrary position j and the repetitive number of the stress applications. Therefore, by deeming that the variation of the stress is a half of a cycle of the stress wave, a consumption $\Delta D_j^{(k)}$ of the shaft life due to the shift from the extreme value $\sigma_j^{(k)}$ to $\sigma_j^{(k+1)}$ is represented by $$\Delta D_j^{(k)} = 1/(2 \cdot N_j^{(k)}) \qquad (12)$$

Accordingly, the variation of the stress at the arbitrary position j of the rotating shaft system is computed according to the equation (8), the extreme values are counted and the consumption $\Delta D_j^{(k)}$ of the duration is computed and accumulated according to the equations (9) to (12).

That is, the resultant accumulation $D_j$ can be represented by $$D_j = \sum_{k}^{n} \Delta D_j^{(k)} = \sum_{k}^{n} 1/(2 N_j^{(k)}) \qquad (13)$$

and it indicates the amount of consumption of the duration until the stress extremes occur (n+1) times at the arbitrary position j on the rotating shaft system.

Accordingly, the fatigue life expenditure is computed by a fatigue life expenditure counting unit (x) composed of extreme value detectors (15) for detecting extreme values $\sigma_j^{(k)}$ (k=1, 2 . . .) of the stress wave $\sigma_j$ and a multiplexer (16) combining data from the extreme value detectors 15 to send them to a computer 17 in which the fatigue life expenditure at the respective arbitrary positions A to H is computed according to the equations (9) to (13).

Reference numerals 18 and 19 show an indicator for indicating the fatigue life expenditure at the respective arbitrary position which is computed by the computer 17 and a memory for recording the indications, respectively. Therefore, the fatigue life expenditure can be determined when the fatigue life expenditure $D_j$ at one arbitrary position j becomes 1.

Decribing a case where a vibration whose stress can not be estimated by the linear decomposition occurs, with reference to FIG. 5, a reference numeral 20 shows an electrical transient detector for detecting an external force exerted on the rotating shaft system Z due to such as a thunder. The electrical transient detector 20 is provided separately from the rotating shaft system Z and positioned to be responded to the external force. A reference numeral 21 shows a delay circuit for regulating the time from the starting of the recording unit 22 to a time at which the rotation of the rotating shaft system is stabilized and a normal recording becomes possible. The delay circuit 21 is connected to the detector Y and the electrical transient detector 20. A reference numeral 23 shows a reference voltage generator for generating a voltage related to a set value $\sigma_s$ and a reference numeral 24 shows a comparator for comparing the stress $\sigma_j$ at the arbitrary position which is obtained by the adders 14 with the above set value $\sigma_s$ to start the operation of the recording unit 22 when $\sigma_s < \sigma_j$. The recording unit 22 records outputs of the electrical transient detector 20 and the detector Y. That is, in this case, the torsional vibration at the certain position P and the external force exerted at that time on the rotating shaft system Z are recorded by the recording unit 22 and thereafter the recorded data are analysed by a large computer according to which the monitoring is performed. Therefore, there is no need of recording all data for a long period of time, resulting in that it is used economically and reliably with minimum expense.

As described hereinbefore, in the embodiment of the present invention, the torsional vibration of the rotating shafts 4 is detected by the detector Y at the certain position P thereon, the detected vibration is decomposed to components of the respective modes inherent to the rotating shaft system Z through the respective decomposing devices 12, the i-th mode stress components at the arbitrary positions j are obtained by the modal arithmetic units 13 and the stresses at the respective arbitrary positions j are calculated by the adders 14. Furthermore, by processing these stresses by the fatigue life expenditure counting unit (x), the fatigue life expenditure at the respective arbitrary positions are calculated. That is, since the rotating shaft system Z is monitored by not obtaining stresses with using pickups mounted on the respective monitoring positions but estimating the stresses at the arbitrary positions on the basis of the monitoring at the certain position, there is no physical limitation on the monitoring positions.

Furthermore, when vibrations, the stresses due to which exceed the set values of the electrical transient detector 20, the comparator 24 and the recording unit 22 and is undesirable to estimate them linearly, occur, the real torsional vibration at the certain position P is recorded and, simultaneously, the external force exerted on the rotating shaft system thereby is also recorded. Therefore, they can be fully analysed by using the large computer in later time. Since there is no need of recording all data for a long period of time, it is inexpensive and economical.

What is claimed is:

1. A torsional vibration monitoring apparatus for a rotating shaft system, comprising a detector for detecting a torsional vibration of the rotating shaft system at at least one certain position thereon, decomposing devices each for decomposing a vibration waveform obtained by said detector to a plurality of components of vibration modes inherent to the rotating shaft system, modal arithmetic units for obtaining stresses each for different ones of said vibration modes at at least one certain position on said rotating shaft system on the basis of a relation between components of the respective vibration modes of the rotating shaft system at the certain position and the arbitrary position thereon and a relation between the vibration and the stress at the arbitrary position, adders each for adding the stresses or different ones of the vibration modes obtained by said modal arithmetic units at the arbitrary position and a fatigue life expenditure counting unit for calculating the fatigue life expenditure of the arbitrary position on the rotating shaft system due to fatigue on the basis of the stress at the arbitrary position, obtained by said adders.

2. A torsional vibration monitoring apparatus as claimed in claim 1, wherein said fatigue life expenditure counting unit comprises extreme value detectors for detecting extreme values of the stress wave, a multiplexer for combining data from said extreme value detectors and a computer for obtaining an estimation of the fatigue life expenditure.

3. A torsional vibration monitoring apparatus as claimed in claim 1, further comprising an electrical transient detector for detecting an external force exerted on the rotating shaft system when a large vibration, the amplitude of which exceeds those capable of being analysed linearly, occurs, a comparator for comparing the stress obtained by said adders at the arbitrary position with a value set previously to provide an instruction when the stress exceeds the set value and a recording unit responsive to the instruction from said comparator for recording vibration waveforms obtained by said detector at the certain position and an output of said external force detector.

* * * * *